(12) United States Patent
Johnson (10) Patent No.: US 11,465,148 B2
(45) Date of Patent: Oct. 11, 2022

(54) METHODS AND APPARATUS FOR FORMING 2-DIMENSIONAL DROP ARRAYS

(71) Applicant: Pattern Bioscience, Inc., Austin, TX (US)

(72) Inventor: Ross Johnson, Austin, TX (US)

(73) Assignee: PATTERN BIOSCIENCE, INC., Austin, TX (US)

(*) Notice: Subject to any disclaimer, the term of this patent is extended or adjusted under 35 U.S.C. 154(b) by 149 days.

(21) Appl. No.: 16/385,029

(22) Filed: Apr. 16, 2019

(65) Prior Publication Data

US 2019/0314819 A1 Oct. 17, 2019

Related U.S. Application Data

(60) Provisional application No. 62/658,172, filed on Apr. 16, 2018.

(51) Int. Cl.
*B01L 3/00* (2006.01)
*G01N 21/64* (2006.01)
(Continued)

(52) U.S. Cl.
CPC .... *B01L 3/502784* (2013.01); *B01F 23/4105* (2022.01); *B01L 3/502707* (2013.01); *B01L 3/502746* (2013.01); *C12Q 1/18* (2013.01); *G01N 21/6452* (2013.01); *G01N 33/5008* (2013.01); *B01F 23/06* (2022.01); *B01F 23/4143* (2022.01); *B01F 23/4145* (2022.01); *B01F 2101/23* (2022.01); *B01L 2200/0636* (2013.01); *B01L 2200/0647* (2013.01); *B01L 2200/0673* (2013.01); *B01L 2200/10* (2013.01);
(Continued)

(58) Field of Classification Search
CPC ........ B01L 3/502784; B01L 3/502707; B01L 3/502746; B01L 2200/0636; B01L 2200/0647; B01L 2200/0673; B01L 2200/10; B01L 2200/12; B01L 2300/0861; B01L 2300/12; B01L 2400/02; B01L 2400/084; B01F 3/0811; B01F 2003/0071; B01F 2003/0834; B01F 2003/0842; B01F 2215/0037; C12Q 1/18; C12Q 2563/159; G01N 21/6452; G01N 33/5008
See application file for complete search history.

(56) References Cited

U.S. PATENT DOCUMENTS 6,673,578 B1 1/2004 Uemori et al.
6,990,290 B2 1/2006 Kylberg et al.
(Continued)

FOREIGN PATENT DOCUMENTS

WO    WO 2003/025113    3/2003

OTHER PUBLICATIONS

U.S. Appl. No. 60/962,426, filed Jul. 26, 2007, Boedicker, et al.
(Continued)

*Primary Examiner* — Jennifer Wecker
*Assistant Examiner* — Oyeleye Alexander Alabi
(74) *Attorney, Agent, or Firm* — Norton Rose Fulbright US LLP (57) ABSTRACT

Certain embodiments are directed to finite step emulsification device and/or methods that combine finite step emulsification with gradients of confinement for the formation of a 2D monolayer array of droplets with low size dispersion.

11 Claims, 5 Drawing Sheets

(51) Int. Cl.
  *C12Q 1/18* (2006.01)
  *G01N 33/50* (2006.01)
  *B01F 23/41* (2022.01)
  *B01F 23/00* (2022.01)
  *B01F 101/23* (2022.01)

(52) U.S. Cl.
  CPC ... *B01L 2200/12* (2013.01); *B01L 2300/0861* (2013.01); *B01L 2300/12* (2013.01); *B01L 2400/02* (2013.01); *B01L 2400/084* (2013.01); *C12Q 2563/159* (2013.01)

(56) References Cited

U.S. PATENT DOCUMENTS

| | | |
|---|---|---|
| 2005/0084923 A1 | 4/2005 | Mueller et al. |
| 2010/0227767 A1 | 9/2010 | Boedicker et al. |
| 2010/0228513 A1 | 9/2010 | Roth et al. |
| 2014/0045704 A1 | 2/2014 | Jovanovich et al. |
| 2015/0267246 A1 | 9/2015 | Baroud et al. |
| 2016/0001289 A1* | 1/2016 | Hung ............... B01L 3/502784 436/180 |
| 2016/0271576 A1* | 9/2016 | Arab ............... B01F 3/0807 |
| 2019/0218497 A1 | 7/2019 | Boedicker et al. |

OTHER PUBLICATIONS

U.S. Appl. No. 61/052,490, filed May 12, 2008, Boedicker, et al.
International Search Report and Written Opinion issued in Corresponding International Application No. PCT/US2019/027636, dated Jun. 26, 2019.
Office Action issued in counterpart Indian Application No. 202037045955 dated Jul. 15, 2022, 5 pages.

* cited by examiner

FIG. 1

| A (um) | B (um) | C (um) | D (um) | E (degrees) | F (um) | G (um) | H (um) |
|---|---|---|---|---|---|---|---|
| 10-200 | 1-20 | 5-80 | 15-110 | 10-80 | 10-200 | 10-1000 | 15-500 |

METHODS AND APPARATUS FOR FORMING 2-DIMENSIONAL DROP ARRAYS

PRIORITY PARAGRAPH

The present application claims priority to U.S. Application 62/658,172 filed Apr. 16, 2018, which is incorporated herein by reference in its entirety.

BACKGROUND OF THE INVENTION

A. Field of the Invention

Embodiments generally concern microfluidic devices. Particular embodiments are directed to microfluidic devices for production of uniform droplet arrays.

B. Description of Related Art

A primary cost driver of a microfluidic system can be a consumable microfluidic circuit portion. In certain aspects each microfluidic circuit can have many very small features that need to be identical in size within about a 1-2 micron variance. Therefore, the manufacturing process needs to be well controlled. Given the microfluidic circuits are consumable, the manufacturing process for the microfluidic circuits needs to be operational for large scale manufacturing.

Masters for molding can be produced generally in two ways. The first is by micro-milling. Micro-milling is a reductive manufacturing process where a computer controlled rotating cutter removes material from a solid block of steel, brass, aluminum or other material. Practically speaking micro-milling can produce features on the order of 10 µm and hold tolerances on the order of +/−1 µm. However, to achieve this range of tolerances you must control cutter wear, and/or vibration and temperature of stock and cutter. These things become more of a problem as the number of features increases and the micro-milling time increases. For example, producing a microfluidic chip master containing 32 microchannels with a tolerance of +/−1 µm using micro-milling cannot be currently done commercially.

Another way to produce a master is to use a lithographic process to etch silicon. The features of the etched silicon are then transferred to metal through an electroplating process. This process is capable of holding+/−1 µm regardless of the number of features because it is not susceptible to factors like tool wear, vibration, and thermal conditions. Standard lithographic methods are limited to features that can be mastered to near 90-degree walls. A ramp or angled region cannot be produced using standard lithography. A ramp can be approximated in lithography by an infinite number of 90-degree steps, but this is cost prohibitive. Numerous etching passes are needed to result in a ramp-like cascade of steps. Such a step-down process for manufacturing a ramp-like structure would significantly impact the cost of mastering.

There remains a need for a microfluidic circuit design and method of manufacturing that can be used to cost effectively produce two-dimensional (2D) droplet arrays that have a low drop size dispersion.

SUMMARY OF THE INVENTION

Certain embodiments provide a solution to the manufacturing problems associated with microfluidic devices for forming substantially uniform drop arrays. In particular, a microfluidic device described herein is designed so that it can be manufactured efficiently and cost effectively by micro-milling and lithographic production methods. By way of example, the inventors have designed a device that performs a process for forming low size dispersion 2D droplet arrays. The device uses a microfluidic circuit having a nozzle, a step emulsification region, ramp region, and an imaging or array region. The device and process produce a 2D droplet array having low size dispersion for a more cost effective and robust analysis.

Embodiments are directed to finite step emulsification combined with gradients of confinement for the formation of a 2D monolayer array of droplets with low size dispersion. In certain aspects unstacked 2D monolayer array of droplets with <3% size dispersion can be produced. Certain embodiments are directed to a microfluidic device configured to form a low size dispersion 2D monolayer array.

Certain embodiments are directed to microfluidic circuits comprising: (a) a drop forming region comprising a channel or nozzle having an inlet for receiving a sample, the channel having a constant cross-sectional area, and an outlet that opens into a step region, the channel or nozzle being 10 to 1000 µm long, and a rectangular cross-section with a height of 1 to 20 µm and a width of 2 to 60 µm; (b) the step region having length extending from the nozzle of 15 to 500 µm, a top and a bottom with a height of between 5 to 80 µm, the top or bottom being substantially continuous with the top or bottom, respectively, of the channel or nozzle and the bottom or top being offset from the bottom or top of the channel or nozzle and substantially parallel with the bottom or floor, or top or ceiling of the channel or nozzle, forming a step region configured for finite step emulsification; (c) a ramp region having an angle of between 10 and 80 degrees relative to the floor or ceiling of the step region (the ramp can be positioned above or below the step region depending on design choice) and a length of 10 µm to 1000 µm, the ramp region starts at the end of the step region and terminates in an imaging region (in certain aspects the ramp starts at a height of 5 to 80 µm (determined by the step region height) and increases to a height of 15 or 110 µm over a horizontal length that is determined by the angle of the ramp); and (d) the imaging region is configured to collect drops as a two-dimensional array and to provide for imaging and evaluation of the two-dimensional drop array. The microfluidic circuit can be fluidly connected to a sample reservoir via a flow path that is configured to provide sample to be received by each nozzle inlet. In certain aspects the flow path is a channel having cross-section with a height of 10 to 200 µm and a width of 10 to 200 µm. The microfluidic circuit can be fluidly connected to a waste reservoir configured to receive sample droplets after analysis. In certain aspects the ratio of the nozzle height to step region height is less that 1:3, in particular 1:2.8. In other aspects the ramp angle is 15 to 45 degrees, particularly 30 degrees. In certain aspects the microfluidic circuit is made of a thermoplastic polymer. In particular aspects the microfluidic circuit is a cyclic olefin polymer or copolymer, polycarbonate, or poly (methyl methacrylate) (PMMA).

In other embodiments the microfluidic circuit can be part of a microfluidic analysis system that is operatively position or connected to an image analysis device. The image analysis device can be configured to detect and analyze fluorescence of droplets in the imaging region of the microfluidic circuit. The imaging device can comprise a camera and a microcontroller.

Certain embodiments are directed to methods of finite step emulsification comprising flowing a dispersed phase through a nozzle having a constant cross-sectional area into a confined step region containing a continuous phase and forming constrained droplets, providing a ramp region having an increasing cross-section area through which the constrained droplets flow forming an unconstrained droplet, where the unconstrained droplets are deposited in an array region and form a two dimensional droplet array having a low size dispersion. In certain aspects the dispersed phase is an aqueous sample. The aqueous sample can be a biological or environmental sample. In other aspects the continuous is immiscible with the disperse phase. The continuous phase can be a fluorocarbon.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or any variation of these terms includes any measurable decrease or complete inhibition to achieve a desired result.

The term "effective," as that term is used in the specification and/or claims, means adequate to accomplish a desired, expected, or intended result.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

In conducting 2-dimensional (2D) array analysis it is beneficial to maximize the number of tests that can be run on a given patient sample and minimize the cost of consumables used for performing the analysis. In certain aspects, a patient sample is ideally assessed for the largest number of relevant antibiotics, or other compounds/characteristics, to determine the susceptibility of, for example, one or more microbes in the patient sample. To maximize the number of relevant queries, a patient sample can be split into a plurality of equal volumes. Each volume is then mixed individually with a test substance, e.g., antibiotic(s), and then introduce into a microfluidic circuit where droplets of that individual volume are then created and analyzed. An individual volume of patient sample can be process on a microfluidic circuit separate from other volumes of the patient sample. In certain aspects 1, 2, 4, 8, 16, 24, 32, 40, 48 or more (including all values and ranges therein) microfluidic circuits can be employed.

Figure 1:
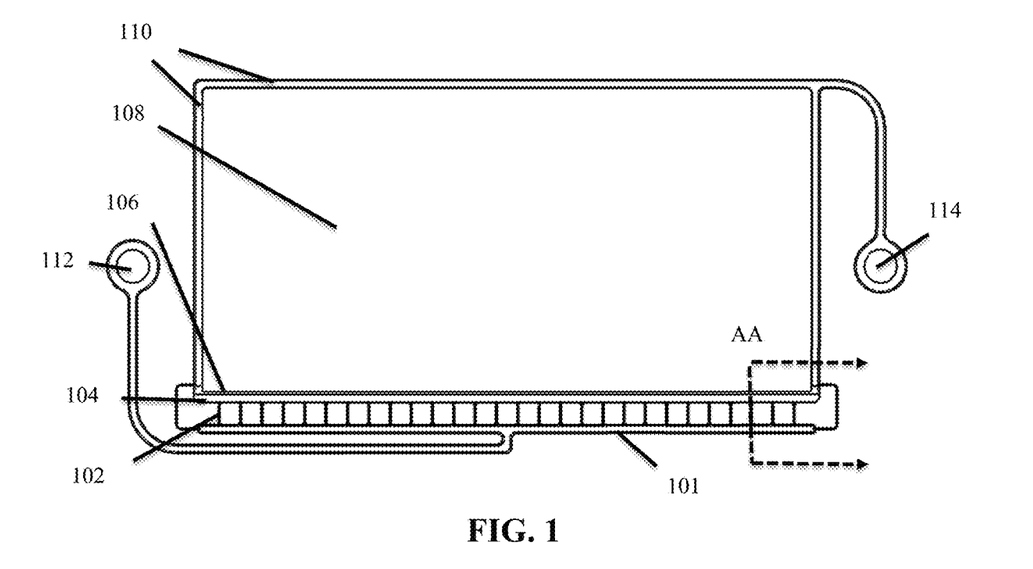
FIG. 1 is an overhead illustration of one example of a microfluidic device designed to produce a 2D monolayer array having a low size dispersion or uniform drop array.

FIG. 1 provides an overhead view of an example of one embodiment of a microfluidic circuit. The circuit comprising the drop forming region including the channels or nozzles 102 fluidly connected to step region 104, that is fluidly connected to ramp region 106 which is in turn connected to imaging area or region 108. Channels 102 are fluidly connected to sample source or reservoir 112 via flow path 101. In certain aspects gutters 110 can be included in the design as well as waste reservoir 114.

Figure 2:
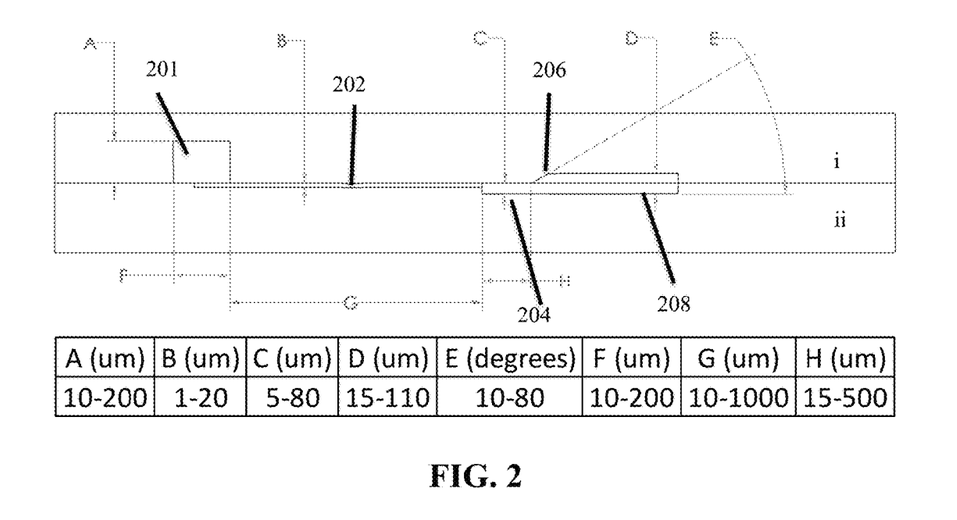
FIG. 2 is a cross section view of one example of a microfluidic device that is produced as a first micro-mill component and a second lithographic component that can be aligned to form a fully integrated microfluidic device.

FIG. 2 depicts cross section AA. Flow path 201 is fluidly connected to channel or nozzle 202. Channel or nozzle 202 flows into step region 204. Step region 204 flows into ramp region 206. Ramp region 206 then flows into imaging region 208. The device can be manufactured in two pieces (i) micro-milled portion and (ii) a lithographically produced portion, which can be fixed together using methods well known in the art to form a microfluidic circuit.

A. MICROFLUIDIC CIRCUITS

In certain embodiments a primary cost driver of a microfluidic system can be a consumable microfluidic circuit portion or microfluidic device/chip/disposable containing a microfluidic circuit. In certain aspects each microfluidic circuit can have many very small features that need to be identical in size within about a 1-2 micron variance. Therefore, the manufacturing process needs to be well controlled. Given the microfluidic circuits are part of a consumable, the manufacturing process for the microfluidic circuits needs to be operational for cost effective, large scale manufacturing. In certain aspects the manufacturing process for the consumable having a microfluidic circuit can be compression injection molding. Like injection molding, compression injection molding replicates the features of a master into a plastic part. The difference is that the compression injection molding allows for much higher precision and smaller features. The part quality produced from compression injection molding is only as good as the master used to form the features. Therefore, a high-quality master is desirable.

Masters can be produced generally in two ways micro-milling and lithography. Micro-milling is a reductive manufacturing process where a computer controlled rotating cutter removes material from a solid block of steel, brass, aluminum or other material. Practically speaking micro-milling can produce features on the order of 10 µm and hold tolerances on the order of +/−1 µm. However, to achieve this range of tolerances you must control cutter wear, and/or vibration and temperature of stock and cutter. These things become more of a problem as the number of features increases and the micro-milling time increases. For example, producing a 32-circuit microfluidic chip master with a tolerance of +/−1 µm using micro-milling cannot be currently done commercially. The fewer the microfluidic circuits per chip the greater the number of chips needed resulting in increased cost.

Lithography is a process for etching silicon. The features of the etched silicon are then transferred to metal through an electroplating process. This process is capable of holding+/−1 µm regardless of the number of features because it is not susceptible to factors like tool wear, vibration, and thermal conditions. Lithographic methods are capable of producing chips having numerous circuits in a chip, limiting the number of consumables to be used. However, standard lithographic methods are limited to features that can be mastered to with near 90-degree walls. In certain embodiments a microfluidic circuit described herein uses a ramp that can be, but is not limited to, between 10 and 50 degrees or so in the microfluidic circuit design. A ramp can be approximated in lithography by an infinite number of 90-degree steps, but this would be cost prohibitive. A step-down process to manufacture a ramp structure would significantly impact the cost of mastering.

In certain embodiments a microfluidic circuit can be manufactured using a two-piece manufacturing process with a first component being generated using compression injection molding or an analogous process where a lithographically generated master is used to form small channels and a single step region, which are structures that are easily and cost effectively produced using lithography. A second component can be generated using compression injection molding or an analogous process using a micro-milled master for those structures that are structures that are cost effectively produced using micro-milling, which includes structures such as but not limited to the ramp region and imaging region. These two components can be aligned and bonded to form a microfluidic circuit as described herein.

Figure 3:
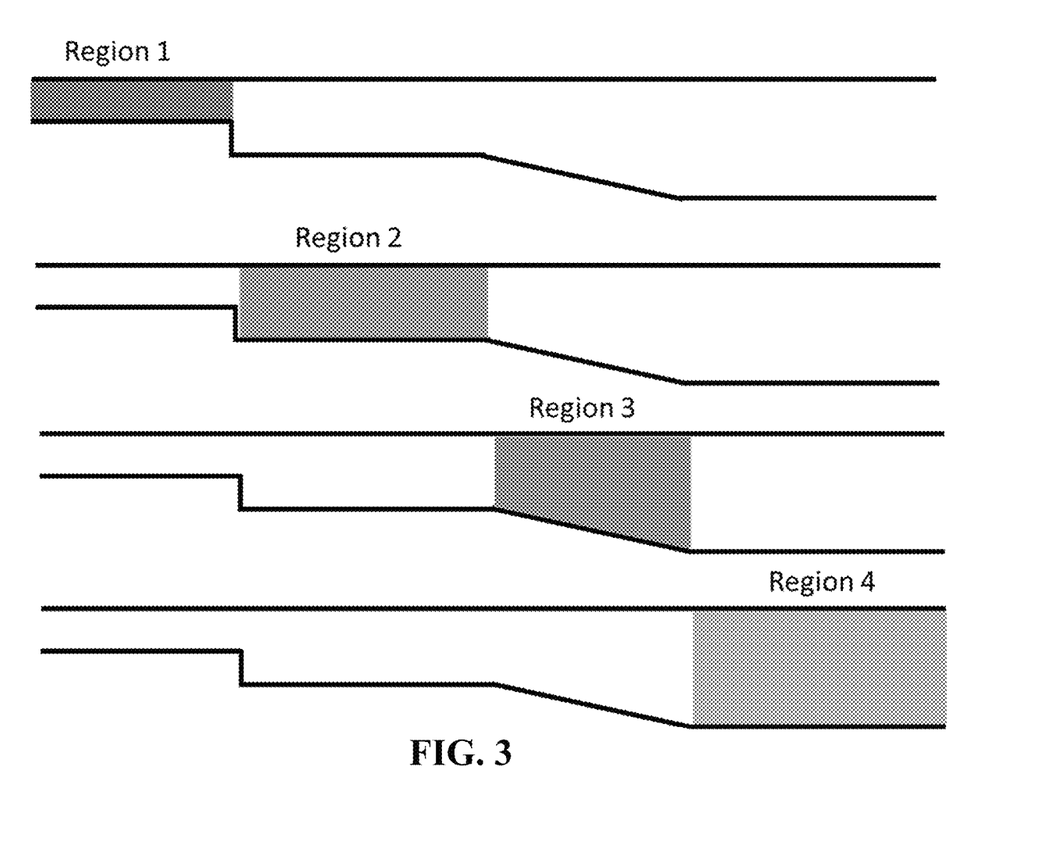
FIG. 3 illustrates four general regions of the microfluidic design: region 1=nozzle, region 2=finite step emulsification region, region 3=ramp region, region 4=imaging or array region.

The alignment precision between a drop formation component (e.g., ii of FIG. 2, region 1 and region 2 of FIG. 3) and an array formation component (e.g., i of FIG. 2, region 3 and region 4 of FIG. 3) can be on the order of +/−50 µm. The alignment need not be tightly controlled because the position of the ramp with respect to the droplet formation features does require 1 to 2 µm precision in order to maintain consistent droplet size. Lithography can be used to form the features of the design that are critical to droplet formation and micro-milling can be used to form the non-critical features relative to drop formation, which are then bonded together to make a microfluidic device having an array of microfluidic nozzles and related circuit that are all essentially identical from a droplet formation perspective. The droplets are formed in a portion of the device produced with a high degree of precision (+/−1 to 2 µm) and the drops finished and processed in a portion of the device that can be produced with a lesser degree of precision (+/−5 to 30 µm).

A device that requires a ramped portion to form the drops (nozzle/ramp configuration) would suffer from issues of alignment because the ramp is integral in forming the drops and must be positioned with much greater precision to form the droplets with a low dispersion. If the ramp was not nearly perfectly aligned with the outlet of the small channels in the nozzle/ramp configuration the droplet size and consistency would be affected. Therefore, a nozzle outlet directly feeding a ramp region would likely see significant variation from part to part if they tried to have more than 1, let alone up to 32, microfluidic circuits in one part. A nozzle/ramp (as contrasted with a nozzle/step/ramp configuration) would be difficult to impossible to produce cost effectively at the tolerances needed.

B. LOW SIZE DISPERSION DROPLET EMULSIONS

There are multiple ways to form low size dispersion droplet emulsions. The most common method is to use a two-phase flow system. This method typically uses the shear stress imparted by a flowing continuous phase to form droplets from a flowing dispersed phase. As the name implies, this method requires both phases to be flowing. Additionally, to maintain low droplet size dispersion one of the flow rates (either continuous or dispersed) requires precision control. Due to the need for two different flow rates, this method requires a more complex system to employ.

Figure 5:
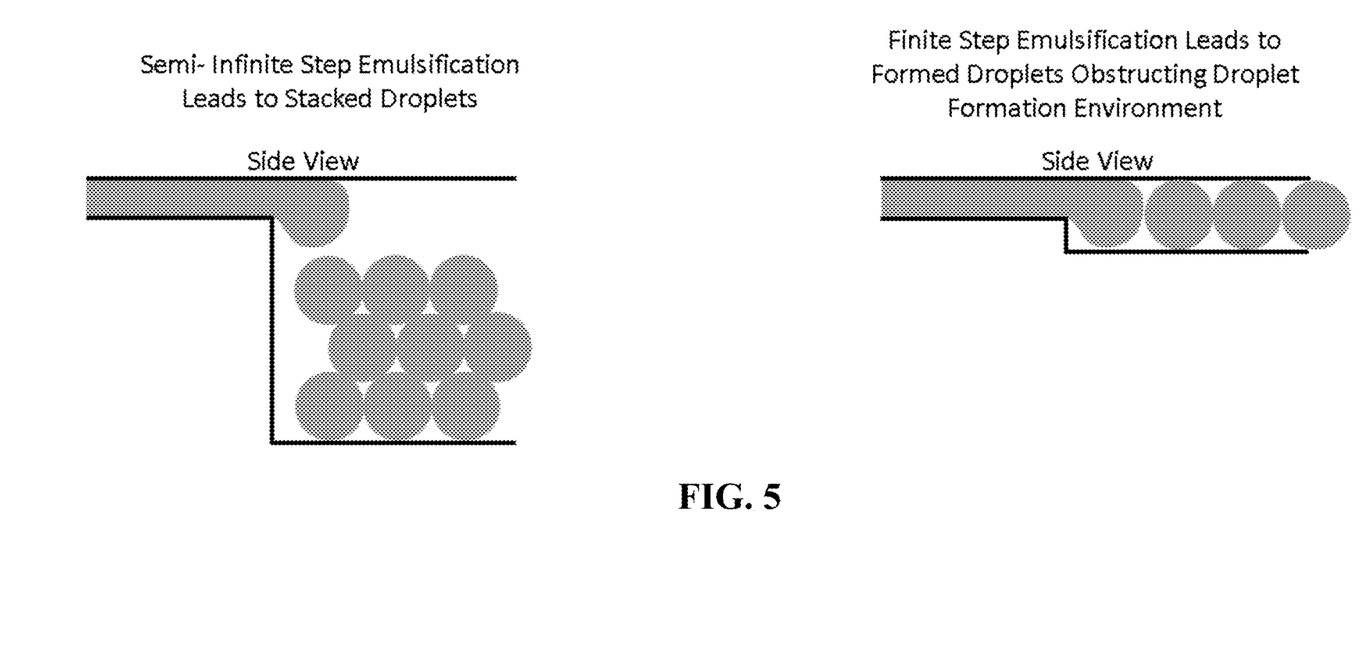
FIG. 5 illustrates some of the issues that can be encountered using current designs to produce small droplet arrays.

Another way to form low size dispersion droplet emulsions is to use single phase flow techniques. In single phase flow systems, the dispersed phase flows while the continuous phase remains static. These systems may use changes in Laplace pressure or buoyancy to induce droplet formation. Although the system complexity is lower with single phase flow compared to two-phase flow, there are other challenges with the single flow method that need to be addressed if the goal is to form a 2-D monolayer array of low size dispersion droplets (see FIG. 5 for a few examples).

One of the first methods to use the single-phase flow technique was step emulsification. Step emulsification can be embodied in two general ways. The first embodiment can be considered as a channel carrying a dispersed phase that is introduced into a semi-infinite step containing a static continuous phase. A semi-infinite step is defined as a step that is significantly greater than 1× the unconfined formed droplet diameter. In this scenario, a droplet will be created by gradients in Laplace pressure. After formation, the droplet may rise, fall, or remain at the nozzle exit depending on the relative buoyancy of the dispersed phase compared to the continuous phase. If the buoyancy is mismatched, the formed droplets will float or sink away from the nozzle until they reach the semi-infinite wall. Droplets formed in semi-infinite step systems have excellent size dispersion due to the consistent environment at the outlet of the nozzle. However, if the droplet production rate is high enough, the droplets will begin to stack at the semi-infinite wall and a 2D monolayer will not be achieved until buoyancy forces the droplets to unstack. Buoyancy is a relatively weak force on picoliter droplets, so unstacking takes a very long time. Additionally, if the stacking is severe, the stacked droplets will eventually crowd at the outlet of the nozzle and obstruct the formation of new droplets. This crowding creates an inconsistent environment at the outlet of the nozzle, and therefore increases the size dispersion. If the buoyancy between dispersed and continuous phases is matched, the droplets will crowd at the outlet of the nozzle and obstruct the formation of new droplets. This crowding increases the droplet size dispersion for reasons mentioned above. The crowded droplets are also free to stack due to the lack of confinement and a 2D monolayer will not be achieved.

The second embodiment of step emulsification can be considered as a channel carrying a dispersed phase (e.g., an aqueous phase) that is introduced into a finite step containing a static continuous phase (e.g., an oil phase). A finite step is defined as a step that is significantly less than 1× the unconfined droplet diameter. In this embodiment the droplet remains compressed after formation, so buoyancy does not play a roll. This embodiment is favorable to the first because it ensures the formed droplets create a 2D monolayer. But because there is no mechanism to clear the formed droplets from the nozzle, the droplets crowd at the outlet of the nozzle and obstruct the formation of new droplets, increasing the size dispersion of the 2D monolayer array formed by a finite step emulsion.

Figure 6:
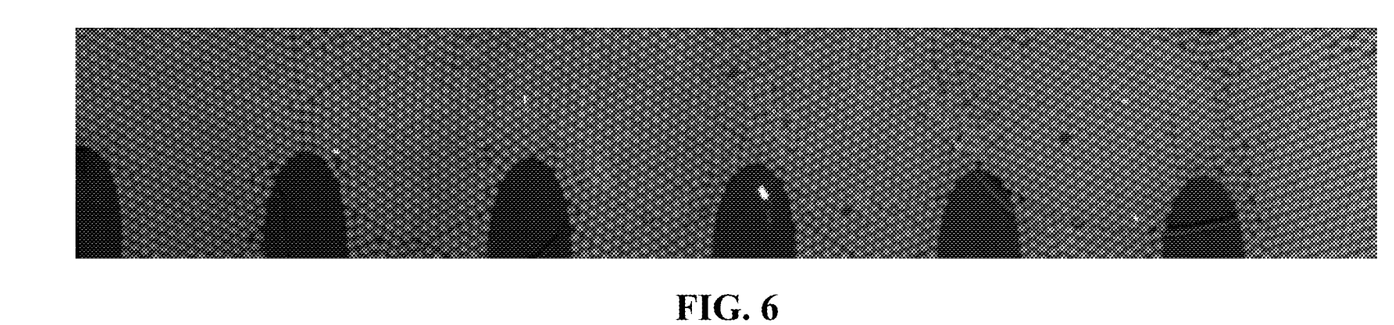
FIG. 6 is a photograph of an array produced using methods described herein. The image has a droplet size dispersion of 2.3% (1456 droplets with a coefficient of variation equal to 2.32%).

The methods described herein combine finite step emulsification with a feature to maintain a consistent environment at the outlet of the nozzle. The result is a 2D monolayer array of droplets with low size dispersion (see FIG. 6 for an example).

Figure 4:
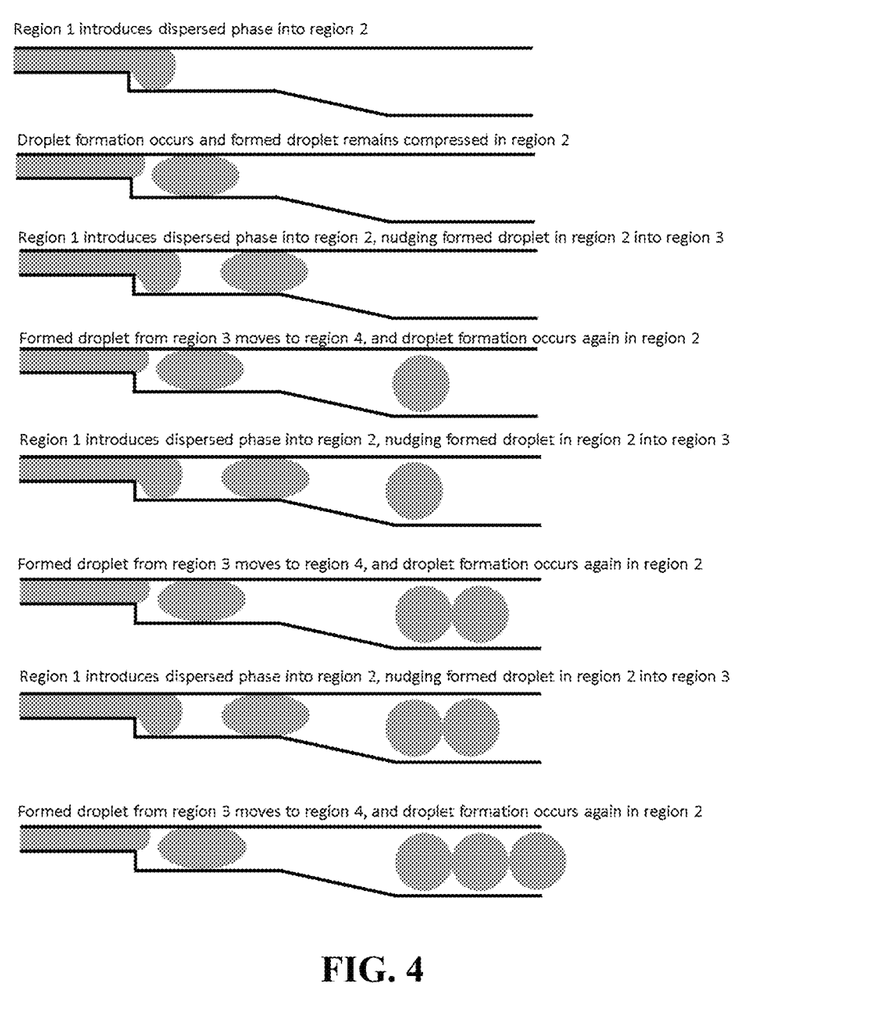
FIG. 4 illustrates one example of drop formation as a sample moves through a microfluidic device.

A research group headed by Charles Baroud from the Ecole Polytechnique has shown a method for creating relatively large low size dispersion 2D monolayer droplet arrays using gradients of confinement. Using their method, they have been able to achieve size dispersions as low as 3% in these relatively large droplets. The method propose here differs from Baroud in that it designed to form much smaller small droplets with a size dispersion significantly better than many of other single-phase flow systems forming a 2D monolayer array of droplets. The current device and methods produce a much smaller droplet than the Baroud method using a microfluidic circuit that is better designed for high volume arrays. The microfluidic circuit design combines four regions (see FIG. 3 and FIG. 4) to create a consistent environment at the outlet of the nozzle during droplet production that results in a 2D monolayer array of droplets with low size dispersion.

C. MICROFLUIDIC DEVICE

In certain embodiments a microfluidic device is designed to produce a 2D droplet array with low size dispersion. In statistics, dispersion or variability is the extent to which a distribution is stretched or squeezed. Common examples of measures of statistical dispersion are the variance, standard deviation, and interquartile range. As used herein low size dispersion refers to dispersion of less than or about 6, 5, 4, 3, 2, or 1%, including values and ranges there between. In certain aspects low size dispersion refers to a dispersion of less than 3%. In particular aspects the droplet size dispersion is about 2.1 to 2.5%, or 2.3%.

The methods and devices described herein create a 2D monolayer array of droplets with low size dispersion by using four processing regions. In certain aspects a device or portion of a device that comprises all four regions operatively coupled as described below is referred to as a microfluidic circuit. A microfluidic device can include 1, 2, 4, 8, 16, 32, 64, 128 or more (including all values and ranges there between) channel regions or nozzles coupled to a second, third and fourth region. In certain aspects all or some of the nozzles will be in fluid contact with a common step, ramp, and array region.

The first processing region is the channel region or nozzle that introduces the dispersed phase. This region has constant cross-sectional area and has the highest surface energy. In certain aspects the cross sectional area can be 1, 50, 100, 150, 200, 250, 300, 350, 400, 450, 500, 550, 600, 650, 700, 750, 800, 850, 900, 950 to 1000 $\mu m^2$, including all values and ranges there between.

The second processing region is the finite emulsion step region. This region has constant cross-sectional area and the second highest surface energy. These two regions (channel/nozzle and finite step) are where droplet formation occurs. The finite step region has a second function which is to hold the formed compressed droplet in place until the channel introduces more of the dispersed phase into the finite step region. This additional dispersed phase nudges the compressed formed droplet that is held in the finite region into the third region. (see for example FIG. 4)

The third processing region is the ramp region. This region has increasing cross sectional area and its surface energy ranges from second highest at the upstream extreme to third highest in the downstream extreme. When the compressed formed droplet enters this region, the droplet will progressively lower its surface energy proportionally by decompressing in the direction of increasing cross sectional area. This change in surface energy acts to propel the droplet through the ramp region downstream into the fourth processing region. This ramp region prevents droplets from the fourth region from back-stacking into the second step region so that the environment in the second step region is consistent and controlled for consistent droplet formation.

The fourth processing region is the collection region where the 2D monolayer is formed. Here the fully formed droplets are at the lowest surface energy. The surface energy in this region is also constant because the cross-sectional area is constant. The monolayer array of droplets grows over time as droplets are added to the region. These four regions combine to create a consistent environment during droplet production that results in a 2D monolayer array of droplets with low size dispersion.

The microfluidic circuit comprising these four regions can be coupled to a sample source through a common flow pathway. The common flow pathway will have an inlet at the proximal end of the path and an outlet or plurality of outlets along the path connected to channel regions/nozzles.

D. METHODS OF ARRAY FORMATION

In certain aspects the droplets are in an immiscible fluid. Upon mixing of a target-containing solution and the immiscible fluid, they form phases—an aqueous drop or partition, which holds the target material in solution, and a non-aqueous or continuous phase made up of the immiscible fluid. The immiscible fluid can be a fluorocarbon comprising a fluorosurfactant or hydrocarbon oils such as mineral oil, or silicone oils. In particular aspects the droplets can be between 0.1 pL and 10 nL. In a further aspect the droplets are at least, at most, or about 0.1. 0.5, 1, 5, 10, 20, 30, 40, 50, 60, 70, 80, 90, or 100 pL to 200, 300, 400, 500, 600, 700, 800, 900, or 1000 pL, including all values and ranges there between. In certain aspects the droplets are about 40 to 300 pL, more particularly are or about 143 pL. In certain aspects the droplets have a diameter of 40, 45, 50, 55, 60, 65, 70, 75, 80, to 85 µm. In particular aspects the droplets are or are about 65 µm. The methods can further comprise arranging the droplets in a 2D array. In certain aspects the two-dimensional array is a static two-dimensional array.

Monitoring of the optical characteristics of the droplets can be performed using a detector, such as a camera or the like. In certain aspects the optical characteristics include fluorescence of the droplets. In certain aspects the monitoring of the optical characteristics of the droplets further comprises illuminating with or exposing the droplets to electromagnetic radiation, such as light. In certain aspects the electromagnetic radiation comprises an excitation wavelength that is compatible with the reporter, i.e., illuminating or irradiating a droplet with an appropriate source. In certain aspects the source provides light including an excitation wavelength of 500, 525, 550, 575, 600, 625, 650, 675, to 700 nm, including all values and ranges there between. The source will be selected so that the electromagnetic radiation excites one or more reporter, e.g., dyes or other compounds. In particular aspect the light source can be a light emitting diode (LED).

Reporters can include a "viability dye" or "reporter dye", the viability or reporter dye is a moiety that detects changes in the environment surrounding an isolated cell due to a cell's viability, respiration, or metabolic activity; or is a detectable protein that is expressed under specific conditions (e.g., green fluorescent protein or luciferase). In certain aspects a cell can be transfected or engineered to express a reporter protein. The reporter can be detected using any method known in the art appropriate to the reporter employed, for example light emission or absorbance of a fluorophore or a colorimetric dye. In certain instances, the signal from the reporter is detected by optical microscopy, camera, or other detector/sensor as appropriate. In certain aspects the reporter is a fluorescent dye. In certain aspects the reporter is resazurin, a resazurin-based dye, or a dye that is a derivative of or structurally related to resazurin (7-Hydroxy-3H-phenoxazin-3-one 10-oxide). Resazurin is a non-toxic, cell permeable compound that, in its oxidized state, is blue in color and virtually non-fluorescent. When in contact with living cells, resazurin is reduced to resorufin, a compound that is red in color and highly fluorescent and can be detected fluorimetrically or colorimetrically. Metabolic activity of viable cells continuously converts resazurin to resorufin, increasing the overall fluorescence and color of the media surrounding cells. A resazurin-based dye is a dye that contains a resazurin structure in addition to other modifying groups. In other aspects a viability dye is tetrazolium, a tetrazolium-based dye, or a dye that is a derivative of or structurally related to tetrazolium. A tetrazolium-based dye is a dye that contains a tetrazolium moiety and may contain other modifying groups that do not disrupt the five membered tetrazolium ring.

In certain aspects the incubating of the droplets is at a constant temperature (isothermal). In other aspects the temperature can be controlled and can be stepped or ramped up using a particular interval or rate, such as stepping up from 25 to 37° C. or increasing at a rate of 2 to 10° C. per minute. In still other aspects temperature can be decreased at a particular interval or rate, such as decreasing at an interval of 5 to 10° C. or a rate of 2 to 10° C. per minute. In various aspects the temperature(s) are in the range of 20 to 45° C., 30 to 40° C., or 35 to 38° C., including all values and ranges there between. In certain aspects partitions are incubated at 37° C.

In particular aspects a droplet can comprise a single cell, microbe, or cellular or microbial aggregation. In a further aspect the droplet may contain 2, 3, 4, or more cell or microbe types. The methods can further comprise classifying a microbe by species, genus, family, order, class, phylum, kingdom, or a combination thereof. The classification can be based on the characteristics of one or more waveforms under one or more conditions. In certain aspects the microbe is bacteria. Certain aspects of the invention can include classifying the bacteria by gram-stain group or other classification criteria recognized for microbes, including bacteria. In certain instances, a droplet may contain more than one target type (species, genus, etc.) but that an environmental stressor or condition may kill all but one target type, which can be identified using its signature or waveform.

The methods can further comprise dividing the sample into at least a control sample and at least one test sample prior to forming a 2D array. Each test sample can be treated or processed in a manner that differs from the control. In certain aspects at least one test sample is contacted with a stressor, cytotoxic, anticancer, antimicrobial compound or condition. In certain aspects individual test samples can be exposed to different concentrations compounds or variations in conditions. In other aspects, a test sample can be exposed to a variety of temperatures, environments, or chemicals that may or may not alter the phenotype of the cells contained in the test sample. In certain aspects a DCC is a pathologic or pathogenic cell, such as a cancer cell.

The methods include evaluating the sample (control and test samples) using a partition waveform (i.e., signal detected over time). In certain aspects evaluating includes comparing the partition waveform to a library of stored or predetermined waveforms (e.g., waveform reference).

Certain embodiments are directed to methods for detecting and characterizing DCCs, such as microbes or cancer cells, in a sample comprising (a) contacting a sample comprising microbes with a reporter, e.g., a viability dye, forming a sample mixture; (b) dividing the sample mixture into at least two portions or samples that include a control sample and at least one test sample; (d) introducing a test compound/substance or an antimicrobial drug to the at least one test sample; (e) partitioning each of the control sample and at least one test sample into droplets forming control sample droplets and test sample droplets, where the droplets comprise on average at most one target microbe or a natural aggregation of microbes; (f) incubating the droplets over time at a specific temperature or temperatures; (g) monitoring optical characteristics of the droplets during the incubation time, wherein the optical characteristics include the amount of optical signal produced by interaction of the reporter with the microbe/cell in the droplet; (h) constructing an optical signal waveform for droplets, e.g., a partition or droplet waveform; (i) classifying the microbe/cell within each droplet using the partition waveform shape; and (j)

comparing partition waveforms between the control sample partition waveforms and the test sample partition waveforms and assessing test compound/substance or antimicrobial drug susceptibility based partition waveform comparison. In certain aspects a test compound can include a small molecule, peptide, a nanoparticle, or a protein. In still other instances a test substance can include bacteriophage and other engineered therapeutics. In other aspects the test compound/substance can be a therapeutic identified as a therapy or engineered as a therapy for other disease conditions, such as cancer (e.g., chemotherapeutic or anti-cancer compound or substance).

As used herein, the term "droplet" refers to a volume of fluid (e.g., liquid or gas) that is a separated portion of a bulk volume. A bulk volume may be partitioned into any suitable number (e.g., $10^2$, $10^3$, $10^4$, $10^5$, $10^6$, $10^7$, etc.) of smaller volumes or droplets. Droplets may be separated by a physical barrier or by physical forces (e.g., surface tension, hydrophobic repulsion, etc.). A droplet may (i) reside upon a surface or (ii) be encapsulated by a fluid with which it is immiscible, such as the continuous phase of an emulsion, a gas, or a combination thereof. A droplet is typically spherical or substantially spherical in shape but may be non-spherical. The shape of an otherwise spherical or substantially spherical droplet may be altered by deposition onto a surface. A droplet may be a "simple droplet" or a "compound droplet," wherein one droplet encapsulates one or more additional smaller droplets. The volume of a droplet and/or the average volume of a set of droplets provided herein is typically less than about one microliter, for example droplet volume can be about 1 µL, 0.1 µL, 10 pL, 1 pL, 100 nL, 10 nL, 1 nL, 100 fL, 10 fL, 1 fL, including all values and ranges there between. The diameter of a droplet and/or the average diameter of a set of droplets provided herein is typically less than about one millimeter, for example 1 mm, 100 µm, 10 µm, to 1 µm, including all values and ranges there between. Droplets may be formed by the devices and methods described herein and are typically monodisperse or substantially monodisperse (differing by less than 6, 5, 4, 3, 2, or 1%).

A test sample comprising at least one target cell can be combined with a viability or reporter dye and partitioned into droplets such that a statistically significant number of droplets contain no more than one target cell or aggregation of cells (some microbial species tend to aggregate into cell clusters or chains). In a preferred embodiment, a viability or reporter dye will be reduced from a non-fluorescent molecule to a fluorescent molecule in the presence of a viable cell and then further reduced to a non-fluorescent molecule if the redox potential in the droplet drops below a certain amount, typically −100 mV. The fluorescent signature generated in each droplet is monitored over time and used to identify and characterize the cell contained within. Further details on the processes of the invention are provided below.

Test Sample. Target cells in the test sample include bacteria, fungi, plant cells, animal cells, or cells from any other cellular organism. The cells may be cultured cells or cells obtained directly from naturally occurring sources. The cells may be obtained directly from an organism or from a biological sample obtained from an organism, e.g., from sputum, saliva, urine, blood, cerebrospinal fluid, seminal fluid, stool, and tissue. Any tissue or body fluid specimen. In one embodiment the test sample includes cells that are isolated from a biological sample comprising a variety of other components, such as non-target cells (background cells), viruses, proteins, and cell-free nucleic acids. The cells may be infected with a virus or another intracellular pathogen. The isolated cells may then be re-suspended in different media than those from which they were obtained. In one embodiment the test sample comprises cells suspended in a nutrient medium that enables them to replicate and/or remain viable. The nutrient media may be defined media with known quantities or all ingredients or an undefined media where the nutrients are complex ingredients such yeast extract or casein hydrolysate, which contain a mixture of many chemical species of unknown proportions, including a carbon source such as glucose, water, various salts, amino acids and nitrogen. In one embodiment, the target cells in the test sample comprise pathogens and the nutrient media comprises a commonly used nutrient broth (liquid media) for culturing pathogens such as lysogeny broth, nutrient broth or tryptic soy broth. In any embodiment the media may be supplemented with a blood serum or synthetic serum to facilitate the growth of fastidious organisms.

Compartmentalization/Partitioning. The methods of the invention involve combining a test sample comprising at least one target cell with a viability or reporter dye and then partitioning the test sample into droplets such that no droplet contains more than one target cell or cell aggregates. The number of droplets can vary from hundreds to millions depending on the application and droplet volumes can also vary between 1 pL to 100 nL depending on the application, but preferably between 25-500 pL with a low size dispersion. Droplet formation occurs when an aqueous or disperse phase, the test sample in this case, is introduced into an immiscible phase, also referred to as the continuous phase, so that each droplet is surrounded by an immiscible carrier fluid. In one embodiment the immiscible phase is an oil wherein the oil comprises a surfactant. In a related embodiment, the immiscible phase is a fluorocarbon oil comprising a fluoro-surfactant. An important advantage to using a fluorocarbon oil is that it is able to dissolve gases relatively well and it is biologically inert. Thus, the fluorocarbon oil used in the methods described herein comprises solubilized gases necessary for cell viability.

Reporters. A variety of reporters may be used with the systems and methods disclosed herein. For example, the at least one small molecule metabolic reporter can be a fluorophore, a protein labeled fluorophore, a protein comprising a photooxidizable cofactor, a protein comprising another intercalated fluorophore, a mitochondrial vital stain or dye, a dye exhibiting at least one of a redox potential, a membrane localizing dye, a dye with energy transfer properties, a pH indicating dye. In a further aspect the reporter can be or include a resazurin dye, a tetrazolium dye, coumarin dye, an anthraquinone dye, a cyanine dye, an azo dye, a xanthene dye, an arylmethine dye, a pyrene derivative dye, a ruthenium bipyridyl complex dye or derivatives thereof. Certain embodiments utilize a resazurin-based dye. Cell viability dyes, which are also included in the term reporter used herein, are used as analysis reagents to identify and characterize individual cells or pathogens encapsulated within droplets. Viability dyes have been used since the 1950's for cell viability purposes. However, these reagents are typically employed in samples that are significantly greater than 1 microliter in volume and/or are used as an endpoint assay to indicate the presence of viable cells. Aspects of the invention use a viability dye in droplets that are between 1 pL and 100 nL, and more specifically 25-500 pL. In the method described here the optical signal generated by the viability dye is concentrated by the small droplet volume and measured and recorded over an incubation time. In droplets containing viable cells, this results in an optical signature that is rapidly generated and has information about the characteristics of the cell encapsulated within the droplets. Combined with an environment stressor, such as an antimicrobial or cytotoxic drug, an additional signature can be generated by monitoring the optical signal of the droplets containing a cell over time. The optical signatures from the cell with and without the environmental stressor can be used to determine the identity and/or characteristics of the cell. Furthermore, the differences between the optical signatures obtained from a species of cells exposed to a drug compared to the optical signatures for same species of target cells that are not exposed to the drug can be used to determine the phenotypic drug resistance profile for the target cells obtained from a test sample. Because these signatures are generated from individual cells encapsulated in droplets, they represent information about the individual characteristics of each cell as opposed to an average characteristic of a population of cells that is generated from a bulk sample containing many cells.

The methods of the invention are compatible with any viability or reporter dye that can be used with live cells (does not require cell lysis). In a preferred embodiment the viability dye is a resazurin-based dye or derivative thereof. When blue, non-fluorescent resazurin is irreversibly reduced to pink and highly fluorescent resorufin it produces a fluorescent signal and a colorimetric shift (from blue to pink). In a preferred embodiment, the fluorescence is used because it offers better sensitivity over colorimetric signal changes. The limited-diffusion confinement within a sub-nanoliter volume of secreted fluorescent molecules quickly concentrates to detectable signal levels and is then detected by the methods described below. Furthermore, resorufin is reversibly reduced to non-fluorescent hydroresorufin if the redox environment dips below a particular redox threshold, usually around −100 mV. The combination of irreversible reduction from resazurin to resorufin and the reversible reduction of resorufin to hydroresorufin and oxidation of hydroresorufin back to resorufin depending on the redox potential of the droplet are what create the unique fluorescence signature over time in droplets that are small enough volume such that redox changes occur quickly in the presence of a single cell or cell aggregate. Examples of commercially available resazurin-based dyes are: AlamarBlue™ (various), PrestoBlue™ (Thermo Fisher Scientific), Cell-titer Blue™ (Promega), or Resazurin sodium salt powder. Dyes that are structurally related to resazurin and can be also be used in the method are: 10-acetyl-3, 7-dihydroxyphenoxazine (also known as Amplex Red™), 7-ethoxyresorufin, and 1,3-dichloro-7-hydroxy-9,9-dimethylacridine-2(9H)-one (DDAO dye). In alternate embodiments dyes that rely on tetrazolium-reduction, such as formazan dyes, can be used as the cell viability indicator. Examples include INT, MTT, XTT, MTS, TTC or tetrazolium chloride, NBT, and the WST series.

Cell (DCC) Aggregates. A preferred application of the invention is towards the diagnosis of microbial infections by identifying the microbes causing the infection and whether or not they are resistant to antimicrobial drugs. Thus, in this application, the DCCs can be single-celled microbes. Some bacteria, however, aggregate naturally into clusters or chains. In these cases, some droplets may comprise an aggregate of cells of the same microbial species (homogenous aggregate) rather than a single microbe. In these cases, the shape of the curve may be affected by the number of cells in the aggregate. However, the stored signature waveforms and call logic that are used to classify the compartmentalized cells can account for such aggregates the same way they can account for single cells. Furthermore, if the embodiment includes antimicrobial susceptibility testing the mixture comprising the antimicrobial drug will exhibit the same cell aggregation characteristics as the mixture that excludes the antimicrobial drug and the comparison will still be accurate. Therefore, while the method of the invention generally comprises isolation of single-cells in each droplet, it necessarily accommodates the case of a single cell species in a homogenous aggregate isolated in the droplet rather individual cells. In the case of cancer disease diagnosis, the target DCCs typically do not aggregate if they are circulating tumor cells. If the cancer cells are obtained from tissue, the tissue is typically disintegrated into individual cells prior to analysis. Therefore, each droplet will contain at most one cell; however, in some instances a cancer aggregate may also be analyzed using the described methods.

Signal Detection. Once the droplets have been generated, they must be presented for analysis by an optical system, sensor, or sensor array. In a preferred embodiment, the droplets are presented in a 2D array so that good thermal control can be maintained, and the droplet signals can be measured simultaneously (at a single instance in time) for many droplets. In the droplets containing target cells, the reporter will produce a concentrated fluorescent signal that will rise above the background droplets that do not contain cells. The concentrated signal of the droplet enables single cell identification in comparable time standard PCR techniques which are the gold standard for fast identification. In certain aspects the signal is detected by exciting a reduced reporter with a specific wavelength of light and collecting the bandpass-filtered, Stokes-shifted light with a camera. The advantage to use imaging techniques is that they can image a droplet array that remains stationary and can therefore easily be monitored over time. Cytometry based methods typically employ endpoint detection instead of real time detection because of the difficulty in keeping track of the moving droplets over time. Another advantage to imaging the array is that all the droplets experience the same reaction conditions at the time of analysis. Therefore, droplet signals can be compared at equivalent time points which is important since signals vary over time. With a cytometry approach, droplets pass by the detector at different times. Therefore, some droplets are incubated longer than others at the time of analysis. Finally, there may be different target cell species in the test sample. For each species, there may be an optimal droplet volume and dye concentration that maximizes signal at a particular time point. If an endpoint method is used, droplet volume and reporter concentrations do not need be controlled to the same degree because time can compensate for sub optimality and different species can be characterized universally within a single dye and droplet concentration.

Multiplexing. The methods described herein include the specific identification of multiple cells from a single test sample. By compartmentalizing single cells into their own isolated droplet, competition for resources between cells is eliminated. Therefore, individual cells that would exist collectively as a minority in a bulk population, now have equal access to nutrients when compared to the majority population of cells which results in a higher sensitivity for low abundance cells in a sample with multiple cells types. The multiplexing limitations for this invention depend on the ability to differentiate viability signatures between different cell types. Most methods for multiplexing require multiple dyes (fluorophores) which, in turn, require multiple sets of LEDs, excitation, and emission filters. Because the analytical methods use shape information, in some instances, rather than spectral information, the method can be used to multiplex many targets with a single dye requiring only one LED, emission filter, and excitation filter, thus simplifying the hardware needed to perform the analysis.

E. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Microchannel fabrication. The droplet array formation experiments were performed in cyclic olefin copolymer (COC) microfluidic circuits. The microfluidic circuits were fabricated by hot-embossing a COC cover lid followed by low temperature bonding with COC film to seal the hot-embossed COC cover lid. The hot embossing master was generated using photolithography. The microfluidic circuit geometry is detailed in FIG. 1. The microchannel droplet generator consists of a microchannel that leads into a well-defined step. The well-defined step then leads into a loosely-defined ramp which in this case is approximated by two additional steps.

Reagents and Experimental Protocol. The experiments were performed using a solution of fluorinated oil with 5% (w/w) PEG-PFPE surfactant as the continuous phase. The dispersed phase was a solution of 10% (w/w) resazurin based dye in water. The microfluidic circuit was filled by introducing 11 µL of the continuous phase to the inlet port. Once the circuit was filled with the continuous phase the outlet was subsequently sealed trapping a compressible air bubble between the continuous phase and the outlet seal. Then 11 µL of the dispersed phase was dispensed into the inlet port. Care was taken to ensure no air was introduced between the dispersed phase and the continuous phase.

The microfluidic circuit was then placed into a sealed system capable of controlling the local pressure while imaging the microfluidic circuit. The system increased the local pressure at a fixed rate to drive the dispersed phase into the microfluidic circuit producing microdroplets at a rate of ~1 droplet per microchannel droplet generator per second.

An image of the formed droplets was taken (see FIG. 6), and the following statistics were computed. Average diameter of droplets=53 µm. Number of droplets=1456. Coefficient of variation on the diameter of droplets=2.3%.

The invention claimed is:

1. A microfluidic circuit comprising:
   a droplet forming region comprising:
   one or more channels, each having:
   an inlet for receiving a sample and an outlet that opens into a step region;
   wherein the channel is rectangular and has a top, a bottom, a height of 1 to 20 µm, and a width of 2 to 60 µm;
   wherein the step region has:
   a top, a bottom, and a height of 5 to 80 µm; and
   a flat region having a length of 30 to 500 µm extending from the channel;
   wherein one of the top and the bottom of the step region is continuous with the top or the bottom, respectively, of the channel, and the other of the top and the bottom of the step region is offset from and parallel to the top or the bottom, respectively, of the channel, such that the step region is configured for finite step emulsification; and
   a ramp region having an angle of 10 to 80 degrees relative to the top or the bottom of the step region, wherein the ramp region terminates in an imaging region having a height of 15 to 110 µm;
   wherein the imaging region is configured to collect droplets as a two-dimensional array and to provide for imaging and evaluation of the two-dimensional droplet array; and
   wherein the one or more channels, the step region, and the ramp region are connected such that fluid cannot flow into the imaging region from the ramp region without first flowing through at least one of the one or more channels.

2. The microfluidic circuit of claim 1, wherein the circuit is fluidly connected to a sample reservoir via a flow path that is configured to provide sample to be received by the inlet of each of the one or more channels.

3. The microfluidic circuit of claim 1, wherein the circuit is fluidly connected to a waste reservoir configured to receive the droplets after analysis.

4. The microfluidic circuit of claim 1, wherein the ratio of the channel height to the step region height is less than 1:3.

5. The microfluidic circuit of claim 1, wherein the ramp region angle is 15 to 45 degrees.

6. The microfluidic circuit of claim 1, wherein the circuit comprises a thermoplastic polymer.

7. The microfluidic circuit of claim 1, wherein the thermoplastic polymer is a cyclic olefin polymer or copolymer, polycarbonate, or poly (methyl methacrylate) (PMMA).

8. A microfluidic analysis system comprising a microfluidic circuit of claim 1 positioned in an image analysis device.

9. The system of claim 8, wherein the image analysis device is configured to detect and analyze fluorescence of the droplets in the imaging region of the microfluidic circuit.

10. The system of claim 8, wherein the image analysis device comprises a camera and a microcontroller.

11. The microfluidic circuit of claim 1, wherein the ramp region angle is approximately 30 degrees.

* * * * *